(12) United States Patent
Eichenholz (10) Patent No.: US 8,992,042 B2
(45) Date of Patent: Mar. 31, 2015

(54) ILLUMINATION DEVICES USING NATURAL LIGHT LEDS

(71) Applicant: Halma Holdings, Inc., Cincinnati, OH (US)

(72) Inventor: Jason M. Eichenholz, Winter Park, FL (US)

(73) Assignee: Halma Holdings, Inc., Cincinnati, OH (US)

( * ) Notice: Subject to any disclaimer, the term of this patent is extended or adjusted under 35 U.S.C. 154(b) by 182 days.

(21) Appl. No.: 13/676,837

(22) Filed: Nov. 14, 2012

(65) Prior Publication Data

US 2013/0120980 A1    May 16, 2013

Related U.S. Application Data (60) Provisional application No. 61/559,385, filed on Nov. 14, 2011.

(51) Int. Cl.
| | |
|---|---|
| *F21V 9/16* | (2006.01) |
| *A61B 1/06* | (2006.01) |
| *F21V 13/14* | (2006.01) |
| *F21V 9/08* | (2006.01) |
| *F21V 9/06* | (2006.01) |
| *A61B 3/00* | (2006.01) |
| *A61B 1/227* | (2006.01) |

(52) U.S. Cl.
CPC . *F21V 13/14* (2013.01); *F21V 9/08* (2013.01); *F21V 9/06* (2013.01); *A61B 1/0653* (2013.01); *A61B 1/0684* (2013.01); *A61B 1/227* (2013.01); *A61B 3/0008* (2013.01); *Y10S 362/804* (2013.01)

USPC ............ 362/231; 362/84; 362/293; 362/572; 362/804

(58) Field of Classification Search
CPC ............... A61B 1/0684; A61B 1/0653; A61B 2019/521; A61C 1/088; F21V 13/14; F21V 9/00; F21W 2131/20; F21Y 2101/02; F21K 9/00
USPC .................. 362/231, 293, 572, 573, 574.804, 362/249.02, 84; 600/249
See application file for complete search history.

(56) References Cited

U.S. PATENT DOCUMENTS

| | | |
|---|---|---|
| 3,356,858 A | 12/1967 | Wanlass |
| 3,847,470 A | 11/1974 | Dederer et al. |
| 3,954,329 A | 5/1976 | Pomerantzeff |
| 4,065,208 A | 12/1977 | Currey |
| 4,514,062 A | 4/1985 | Fitzgerald |
| 4,538,888 A | 9/1985 | Sigelman |

(Continued)

OTHER PUBLICATIONS

Zhou, "Key Metrics for Understanding Color Quality for LED Lighting"—Synopsys, Inc., Feb. 27, 2012, p. 1.

(Continued)

*Primary Examiner* — Peggy Neils
(74) *Attorney, Agent, or Firm* — Dinsmore & Shohl LLP (57) ABSTRACT

A method and apparatus are disclosed for a LED used in a medical device emitting a wavelength from about 200 nanometers to about 440 nanometers along a path. A composition of phosphors coats the LED to broaden the electromagnetic spectrum from about 200 nanometers to about 780 nanometers. A filter is positioned in the path to selectively permit electromagnetic radiation of a particular range of wavelengths to pass through. The medical device is used to provide a broad spectral source for medical diagnosis.

27 Claims, 9 Drawing Sheets

(56) References Cited

U.S. PATENT DOCUMENTS

| | | | |
|---|---|---|---|
| 4,963,014 A | 10/1990 | Heine et al. | |
| 5,108,938 A | 4/1992 | Solomon | |
| 5,252,999 A | 10/1993 | Sukigara et al. | |
| 5,436,492 A | 7/1995 | Yamanaka | |
| 5,711,889 A | 1/1998 | Buchsbaum | |
| 5,841,509 A | 11/1998 | Harooni et al. | |
| 5,844,264 A | 12/1998 | Shinji | |
| 5,894,943 A | 4/1999 | Liu | |
| 6,084,229 A | 7/2000 | Pace et al. | |
| 6,089,716 A | 7/2000 | Lashkari et al. | |
| 6,152,873 A | 11/2000 | Rogers | |
| 6,186,944 B1 | 2/2001 | Tsai | |
| 6,202,784 B1 | 3/2001 | Alatriste | |
| 6,350,031 B1 | 2/2002 | Lashkari et al. | |
| 6,383,133 B1 | 5/2002 | Jones | |
| 6,511,420 B1 | 1/2003 | Farrell et al. | |
| 6,638,668 B2 | 10/2003 | Buchsbaum et al. | |
| 6,700,690 B1 | 3/2004 | Buchsbaum et al. | |
| 6,711,426 B2 | 3/2004 | Benaron et al. | |
| 6,909,591 B2 | 6/2005 | Erickson et al. | |
| 7,140,730 B2 | 11/2006 | Wei et al. | |
| 7,149,033 B2 | 12/2006 | Buchsbaum | |
| 7,267,719 B2 | 9/2007 | Lunden et al. | |
| 7,267,787 B2 | 9/2007 | Dong et al. | |
| 7,267,887 B2 | 9/2007 | Kitahara et al. | |
| 7,276,025 B2 | 10/2007 | Roberts et al. | |
| 7,336,757 B2 | 2/2008 | Yoshimura et al. | |
| 7,354,395 B2 | 4/2008 | Lawlis et al. | |
| 7,399,275 B2 | 7/2008 | Goldfain et al. | |
| 7,414,655 B2 | 8/2008 | Meisenzahl | |
| 7,430,048 B2 * | 9/2008 | Reel et al. | 356/432 |
| 7,488,102 B2 * | 2/2009 | Brukilacchio | 362/573 |
| 7,533,992 B2 | 5/2009 | Williams | |
| 7,595,660 B2 | 9/2009 | Grant | |
| 7,646,032 B2 | 1/2010 | Radkov et al. | |
| 7,648,808 B2 | 1/2010 | Buchsbaum et al. | |
| 7,862,173 B1 | 1/2011 | Ellman | |
| 7,887,719 B2 | 2/2011 | Dong et al. | |
| 7,901,351 B2 | 3/2011 | Prescott | |
| 7,915,627 B2 | 3/2011 | Li | |
| 7,922,327 B2 | 4/2011 | Su et al. | |
| 7,999,845 B2 | 8/2011 | Abe | |
| 8,004,560 B2 | 8/2011 | Sato et al. | |
| 8,016,751 B2 | 9/2011 | Weigel et al. | |
| 8,016,753 B2 | 9/2011 | Sugita | |
| 8,021,293 B2 | 9/2011 | Dejima et al. | |
| 8,021,295 B2 | 9/2011 | Morishita et al. | |
| 8,021,301 B2 | 9/2011 | Satoh | |
| 8,022,979 B2 | 9/2011 | Miyamoto et al. | |
| 8,409,081 B2 * | 4/2013 | Takahashi | 600/177 |
| 8,506,478 B2 * | 8/2013 | Mizuyoshi | 600/178 |
| 2005/0043591 A1 | 2/2005 | Witte | |
| 2005/0254237 A1 * | 11/2005 | Nath et al. | 362/190 |
| 2006/0027781 A1 | 2/2006 | Dong et al. | |
| 2007/0052961 A1 | 3/2007 | Lane | |
| 2007/0121071 A1 * | 5/2007 | Jackson et al. | 351/246 |
| 2008/0045800 A2 | 2/2008 | Farr | |
| 2008/0073616 A1 | 3/2008 | Dong et al. | |
| 2008/0252197 A1 | 10/2008 | Li et al. | |
| 2008/0262316 A1 * | 10/2008 | Ajima et al. | 600/178 |
| 2009/0096989 A1 | 4/2009 | Church et al. | |
| 2009/0153797 A1 * | 6/2009 | Allon et al. | 351/206 |
| 2009/0189513 A1 | 7/2009 | Lane | |
| 2010/0002428 A1 | 1/2010 | Hall et al. | |
| 2012/0008093 A1 * | 1/2012 | Spaide | 351/206 |
| 2012/0232345 A1 | 9/2012 | Levy et al. | |
| 2012/0249925 A1 * | 10/2012 | Yang | 349/65 |

OTHER PUBLICATIONS

Midolo et al., "Lighting for clinical observation of cyanosis"—Article, The Australian Hospital Engineer, vol. 30—No. 2, pp. 1-5.
Cheng et al., "Pure white hybrid light-emitting device with color rendering index higher than 90"—Optics Letters, vol. 35, No. 5, Mar. 1, 2010; 2010 Optical Society of America, pp. 616-618.
Beijing Yuji, "High CRI LED Lighting"—High CRI LED lighting Supplier / Beijing Yuji International, Oct. 24, 2013, pp. 1-7.
Opto drive, "Optodrive LED Modules comply with Cyanosis Observation Index (COI) directive"—Press Release, Optoga AB, Sweden, www.optodrive.se/Pressrelease5.pab, pp. 1-2.

* cited by examiner

ILLUMINATION DEVICES USING NATURAL LIGHT LEDS

CROSS REFERENCE TO RELATED APPLICATIONS

The present application hereby claims priority under 35 U.S.C. §119(e) to Provisional U.S. Application No. 61/559,385 filed Nov. 14, 2011, entitled "Illumination Devices and Methods of Using the Same."

TECHNICAL FIELD

The present disclosure relates to apparatus and methods of using an illumination device comprising one or more white lights for medical diagnostic illumination or examination illumination.

SUMMARY

An illumination device is disclosed with at least one light emitting diode emitting electromagnetic radiation with a wavelength from about 200 nanometers to about 440 nanometers. The electromagnetic radiation is emitted along a path. A composition of phosphors coat the at least one light emitting diode. The composition of phosphors may comprise a red phosphor, yellow phosphor, a blue phosphor, a green phosphor, an orange phosphor, a violet phosphor, or combinations thereof. At least one wavelength selection device positioned in the path to selectively permit electromagnetic radiation of a particular range of wavelengths to pass through. A mirror to change a direction of the path and at least one lens to diverge the electromagnetic radiation are included where the at least one wavelength selection device, the minor, and the at least one lens are disposed in the path. The at least one light emitting diode, the wavelength selection device, the minor, and the at least one lens are attached to and within a housing.

A method of illuminating a specimen is disclosed, which includes emitting electromagnetic radiation along a path with a wavelength from about 200 nanometers to about 440 nanometers using at least one light emitting diode, selectively permitting electromagnetic radiation of a particular range of wavelengths to pass through a wavelength selection device disposed in the path, changing the direction of the path using a mirror, and diverging the electromagnetic radiation using a lens, wherein the wavelength selection device, the minor, and the lens are disposed in the path. The at least one light emitting diode is coated with a composition of phosphors comprising a red phosphor, yellow phosphor, a blue phosphor, a green phosphor, an orange phosphor, a violet phosphor, or combinations thereof.

A method of producing electromagnetic radiation is disclosed, including illuminating a specimen using an illumination device and actuating a second adjustment wheel to change the particular range of wavelengths permitted by the at least one wavelength selection device, wherein the illumination device comprises at least one light emitting diode emitting electromagnetic radiation with a wavelength from about 200 nanometers to about 440 nanometers along a path, a composition of phosphors coat the at least one light emitting diode, at least one wavelength selection device positioned in the path to selectively permit electromagnetic radiation of a particular range of wavelengths to pass through, a mirror to change a direction of the path, a lens to diverge the electromagnetic radiation, and a housing, wherein the composition of phosphors may comprise a red phosphor, yellow phosphor, a blue phosphor, a green phosphor, an orange phosphor, a violet phosphor, or combinations thereof, wherein the at least one wavelength selection device, the mirror, and the at least one lens are disposed in the path, and wherein the at least one light emitting diode, the wavelength selection device, the minor, and the at least one lens are attached to and within a housing.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

The present disclosure includes an illumination device that includes a light source that emits approximately white light (wavelengths from about 380 nanometers to about 780 nanometers) and may be used in medical diagnostic or examination procedures. More particularly, the present disclosure describes an illumination device comprising one or more light sources such as, for example, light emitting diodes ("LED") pumped with electromagnetic radiation generally within the ultraviolet ("UV") range and/or near the ultraviolet range ("NUV") of the electromagnetic spectrum used in medical diagnostic illumination or examination illumination.

Color rendering refers to the way that a lamp or other light source affects the way that an object's color is seen. The characteristics of the light source are called color rendering properties. Generally, when a light source has good color rendering properties, it means that it can illuminate objects without changing their natural colors. A more technical description of color rendering is defined as the "effect of an illuminant on the color appearance of objects by conscious or subconscious comparison with their color appearance under a reference illuminant".

The CIE Color Rendering Index (CRI) is the only internationally-accepted metric for assessing the color rendering performance of light sources. In the calculation of the CRI, the color appearance of 14 reflective samples is simulated when illuminated by a reference source and the test source. The reference source is a Planckian radiator (if below 5000 Kelvin) or a CIE Daylight source (if at or above 5000 Kelvin), matched to the correlated color temperature (CCT) of the test source. After accounting for chromatic adaptation with a Von Kries correction, the difference in color appearance ΔE for each sample between the two light sources is computed in CIE 1964 W*U*V* uniform color space. The special color rendering index ($R_i$) is calculated for each reflective sample by:

$$R_i = 100 - 4.6\Delta E_i \quad (1)$$

The general color rendering index ($R_a$) is simply the average of R for the first eight samples, all of which have low to moderate chromatic saturation:

$$R_a = \frac{1}{8}\sum_{i=1}^{8} R_i \quad (2)$$

A perfect score of 100 represents no color differences in any of the eight samples under the test and reference sources. For the visible spectrum, a score of 100 indicates a spectral distribution of wavelengths from about 380 nanometers to about 780 nanometers.

The CRI method specifies that the CCT of the reference source be matched to that of the test source, which assumes complete chromatic adaptation to the chromaticity of the light source. This assumption fails at extreme CCTs, however. For example, a 2000 K (very reddish) blackbody source achieves $R_a$=100, as does a daylight spectrum of 20,000 K (very bluish). However, neither of these sources renders colors well. None of the eight reflective samples used in the computation of $R_a$ are highly saturated. This is problematic, especially for the peaked spectra of white LEDs. Color rendering of saturated colors can be very poor even when the $R_a$ value is good. Further, by optimization of lamps' spectra to the CRI, $R_a$ values can be made very high while actual color rendering is much poorer. This is because the eight color samples used in the calculation of $R_a$ are all of medium saturation and the number of samples is too few.

The eight special color rendering indices are combined by a simple averaging to obtain the general color rendering index. This makes it possible for a lamp to score quite well, even when it renders one or two colors very poorly. Standard white LEDs are at an increased risk of being affected by this problem, as their peaked spectra are more vulnerable to poor rendering in certain areas of color space. Finally, the very definition of color rendering is flawed for many applications. Color rendering is a measure of only the fidelity of object colors under the illuminant of interest and any deviations of object color appearance from under a blackbody source is considered bad. Due to this constraint, all shifts in perceived object hue and saturation result in equal decrements in CRI score. In practical application, however, increases in chromatic saturation, observed when certain sources illuminate certain surfaces, is considered desirable. Increases in saturation yield better visual clarity and enhance perceived brightness.

As discussed above the current CRI metric is based on only eight reflective samples, all of which are low to medium chromatic saturation. These colors do not adequately span the range of normal object colors. Some lights that are able to accurately render colors of low saturation perform poorly with highly saturated colors. This is particularly prominent with light sources with peaked spectral distributions as realized by solid-state lighting. Additionally, the CRI penalizes lamps for showing increases in object chromatic saturation compared to reference lights, which is actually desirable for many applications.

Figure 1:
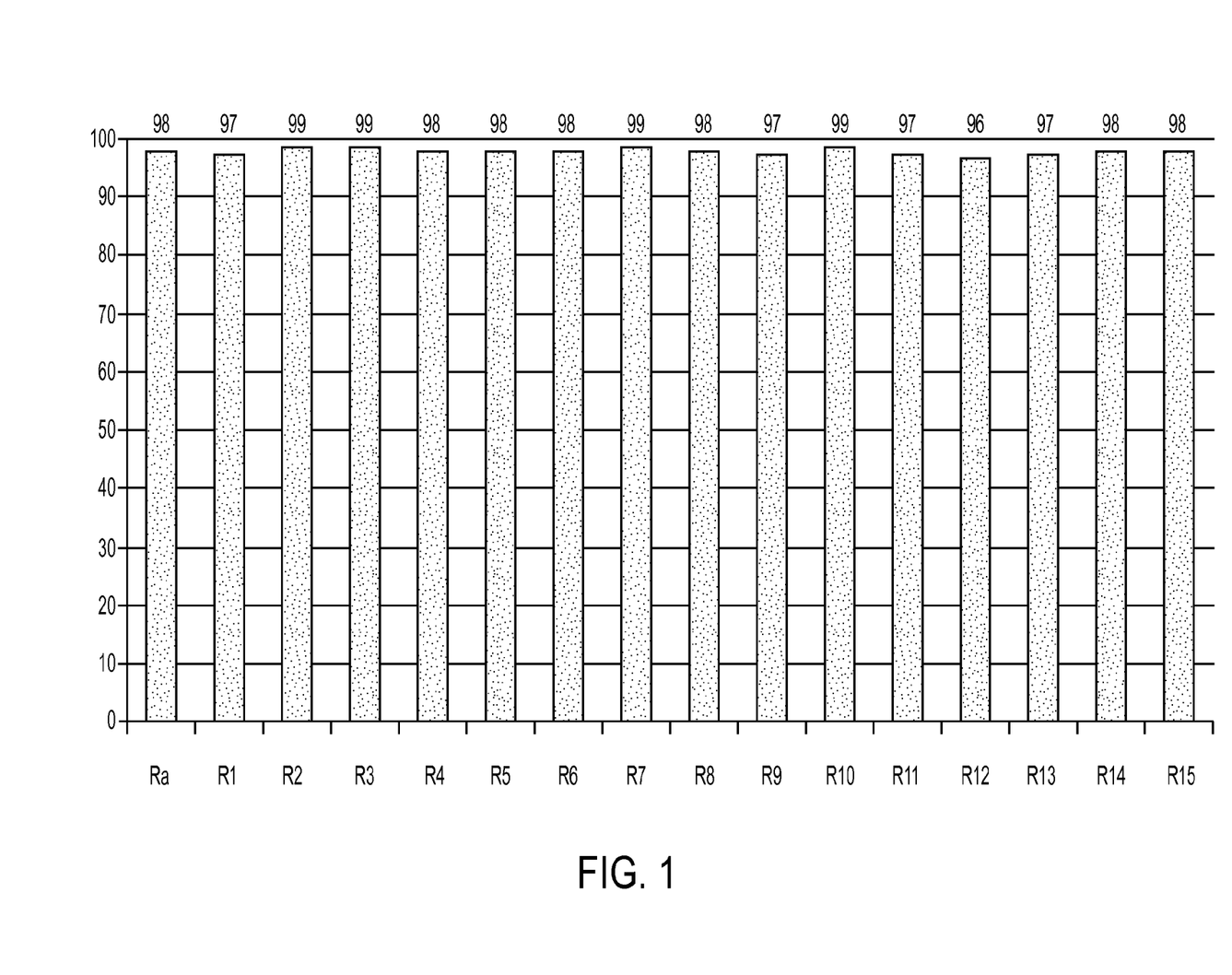
FIG. 1: An illustration depicting the CRI scoring of a UV/NUV pumped illumination device according to one or more embodiments herein.

Rather than assess only color fidelity, this improved metric is intended to assess overall color quality of light sources and is aptly named Color Quality Scale (CQS) to avoid confusion with the CRI. One of the most serious problems with the CRI is that color rendering of saturated colors can be very poor even when the Ra value is good. For the CQS, the eight samples used in the calculation of R have been replaced with 15 samples of high chromatic saturation spanning the entire hue circle. FIG. 1 illustrates a UV and/or NUV pumped LED with a CRI score of $R_a$=98 (R1–R8). A score of $R_a$=97 (R1–R15) (not shown) is achieved using the CQS standard.

It should be understood that the scoring of the LED spectral distribution properties are not limited by the CRI/CQS scoring standards. Any scoring standard may be used to rate the electromagnetic spectrum of the LED. Those LEDs that produce near to or reproduce blackbody incandescent light or sunlight are the subject of this disclosure. For example, the illumination devices and methods shown and disclosed herein using UV and/or NUV pumped LED's are operable to produce a CRI score of about greater than 80%, about greater than 90%, about greater than 95%, greater than about 96%, greater than about 97%, greater than about 98%, greater than about 99%, from about 97% to about 99%, or about 100%. This high color rendering achieves subtle color expressions that were considered impossible with conventional LED's. The medical evaluations would thus be enhanced by the UV and/or NUV LED illumination devices and methods using the same of the present disclosure.

Figure 2:
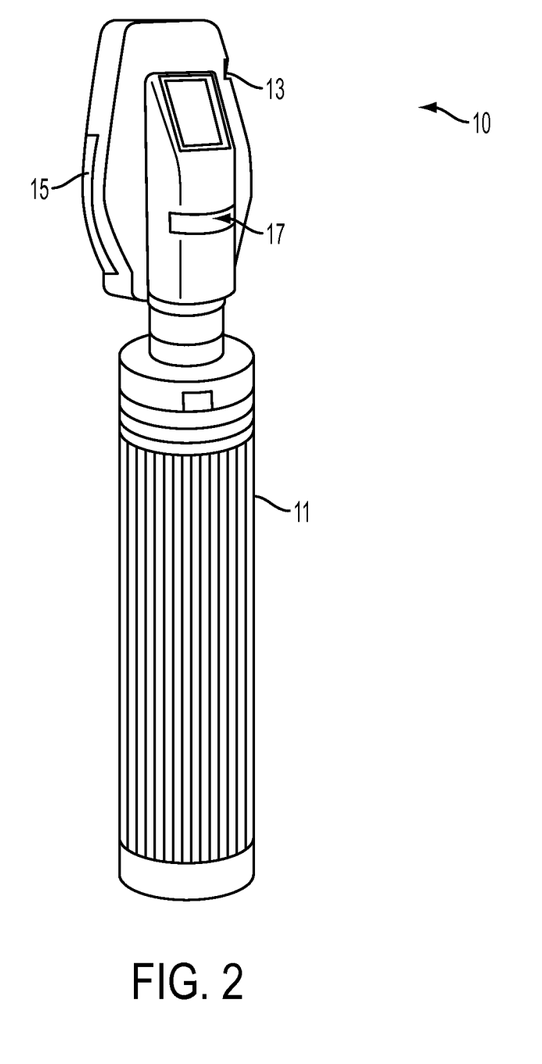
FIG. 2: A perspective view of an illustrative ophthalmoscope according to one or more embodiments herein.
Figure 3:
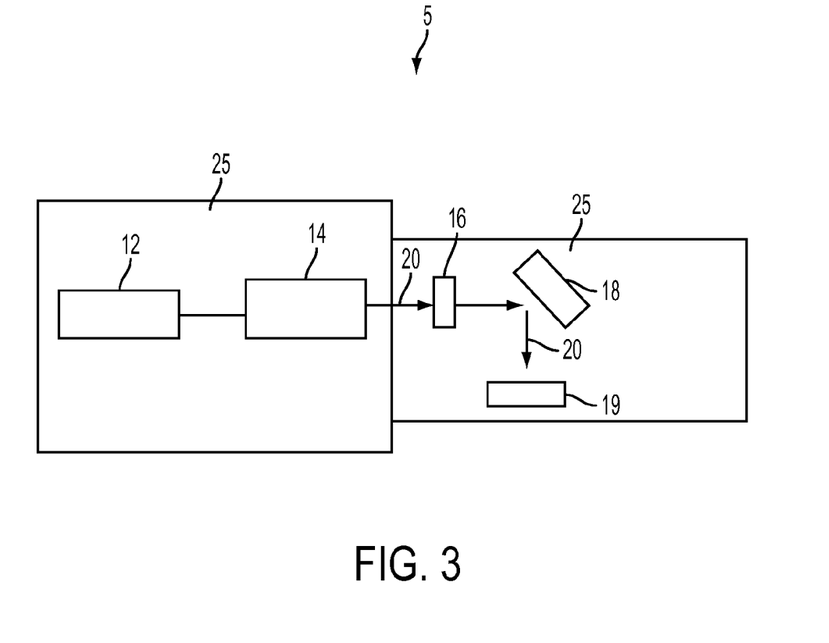
FIG. 3: A schematic diagram of the ophthalmoscope of FIG. 1.

FIGS. 2 and 3 illustrate an illumination device 5 housed in an ophthalmoscope 10. The ophthalmoscope 10 comprises a base housing 11, a head 13, a first adjustment wheel 15, and a second adjustment wheel 17. The base housing 11 may house a battery (e.g., power source 12, FIG. 3). The illumination device 5 may include a power source 12, a LED 14, a wavelength selective device 16, a mirror 18, and/or a lens 19. The first adjustment wheel 15 may be operable to switch to a different lens of the lens 19 and the second adjustment wheel 17 may be for adjusting or changing the particular range of wavelengths permitted by the wavelength selection device 16. The ophthalmoscope 10 may be used to observe and diagnose a retina (not shown) of a patient. It is understood that in this illustrative embodiment and/or in any other embodiments shown and described herein, the illumination device 5 may include one or more of the lens 19, the wavelength selection device 16, mirros, and/or any other components.

The illumination device 5 may have a housing 25 wherein the LED 14, the wavelength selection device 16, the mirror 18, and the lens 19 may be attached to and/or within. FIG. 3 is illustrative of the illumination device 5 and one embodiment of the attachment configuration within the housing 25 but it should not be viewed as limiting. The LED 14 may emit electromagnetic radiation, along a path 20. The mirror 18 maybe used to change a direction of the path 20 to better optimize the path 20 within the housing 25. It should be understood that more than one minor 18 may be used. The lens 19 may be used to diverge the electromagnetic radiation from the LED 14 onto the specimen that is being observed. It should be understood that more than one lens 19 and more than the wavelength selection device 16 may be used. The wavelength selection device 16, the mirror 18, and the lens 19 are disposed in the path 20.

The LED 14 of the illumination device 5 may be an UV and/or NUV pumped LED and may emit electromagnetic radiation with a wavelength from about 200 nanometers to about 440 nanometers, particularly from about 300 nm to about 440 nm, particularly from about 300 nm to about 430 nm, more particularly, from about 300 nm to about 425 nm, more particularly, from about 325 nm to about 415 nm, more particularly from about 370 nm to about 410 nm, more particularly from about 370 nm to about 405 nm, or even more particularly at about 405 nm.

A composition of phosphors may coat the LED 14 either inside or outside of the LED housing. The composition of phosphors may comprise a red phosphor, yellow phosphor, a blue phosphor, a green phosphor, an orange phosphor, a violet phosphor, or combinations thereof. Depending on the color (i.e. wavelength) of the LED 14, phosphors of different colors may be applied to or coat the LED 14 to modify the emitted electromagnetic radiation spectrum which is reflected in the spectrum and CRI value. If several phosphor materials of distinct colors are mixed and applied such as, for example, red (e.g. $(Sr,Ca)AlSiN_3:Eu^{2+}$), and green (e.g. $Ba_3Si_6O_{12}N_2$: $Eu^{2+}$) and/or yellow, the emitted electromagnetic radiation spectrum is broadened, effectively raising the CRI value of the given LED 14 to much greater levels than possible with only the emitted electromagnetic radiation spectrum of the given LED 14 alone.

In some embodiments, the composition of phosphors may be modified to absorb electromagnetic radiation instead of produce electromagnetic radiation to narrow the spectrum of emitted light. The composition of phosphors may allow filtering of the UV and/or NUV electromagnetic spectrum without the need for a dedicated wavelength selection device 16. The compositions of phosphors may absorb electromagnetic radiation with a wavelength of from about 300 nanometers to about 440 nanometers, preferably from about 200 nanometers to about 300 nanometers, and more preferably from about 200 nanometers to about 440 nanometers.

In another embodiment, the composition of phosphors may be added to shift the electromagnetic spectrum to a CRI value of around 100% or natural sunlight which is ideally suited to provide maximum color representations of the specimens being illuminated for medical diagnosis or examination. The composition of phosphors types and amounts used in the UV and/or NUV LED's may be manipulated (by adding and/or subtracting the phosphor and/or different types of phosphors) to optimize the contrast of the specimen illuminated by the LED and/or to customize the spectrum (i.e., a non-uniform spectrum) to meet a specific need. For example, a diseased area on a specimen may be more apparent when illuminated with an electromagnetic spectrum emphasizing specific wavelengths. In another example, the composition of phosphors may be optimized for maximum visualization of the specimen (e.g. retina) and provide maximum contrast.

Still referring to FIG. 3, the wavelength selection device 16 positioned in the path 20 to selectively permit electromagnetic radiation of a particular range of wavelengths to pass through. The particular range of wavelengths may be from about 200 nanometers to about 380 nanometers and/or from about 380 nanometers to about 750 nanometers. Illustrative wavelength selective devices 16 include, but are not limited to, dichroic filters, dichroic mirrors, dichroic reflectors, reflective filters, thin film filters, interference filters, gel film filters, band pass filters, interference bandpass filters (e.g., exciter filters, barrier filters, etc.), any other optical, color filtering, or interference devices, or combinations thereof. The wavelength selective device 16 is optionally a very accurate color filter used to selectively pass light of certain wavelengths (e.g., visible light), while reflecting or absorbing light of other wavelengths (e.g., UV and/or NUV light). Additionally, wavelength selective devices 16 may be a part of, optically connected to, or used with the illumination device 5.

Furthermore, the LED 14 may be arranged in an array (not shown). The array may be chosen from a linear array, a stagger array, a herringbone array, a honeycomb array, a triangular array, a hexagonal array, or a circular array. Further embodiments could feature high brightness white LED's, high power white LED's, cold white LED's or a plurality of white LED's.

Figure 4:
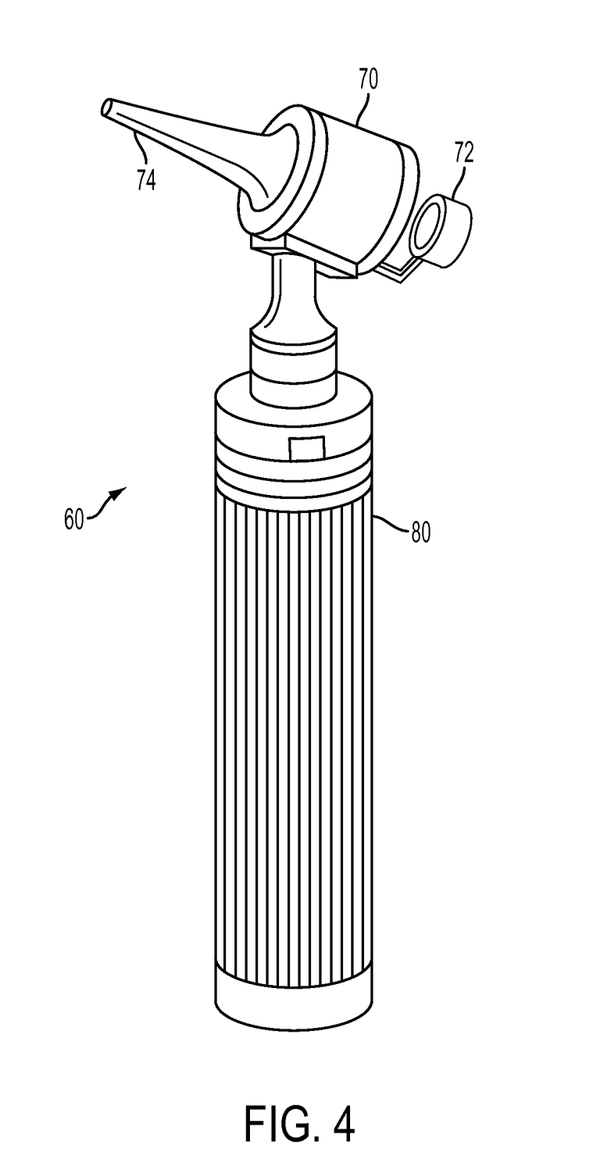
FIG. 4: A perspective view of an otoscope according to one or more embodiments herein.

Referring to FIG. 4, illustrates an otoscope 60 comprising the illumination device 5 (e.g., shown in FIGS. 2-6) that includes the LED 14 pumped with UV and/or NUV and the composition of phosphors e.g., red, green, and blue phosphor as described above. The otoscope 60 may comprise a head assembly 70 and a body assembly 80. The head assembly 70 may further comprise a lens assembly 72 and a speculum component 74. It is understood that the otoscope 60 may include one or more components of conventional otoscopes without departing from the present disclosure.

Figure 5:
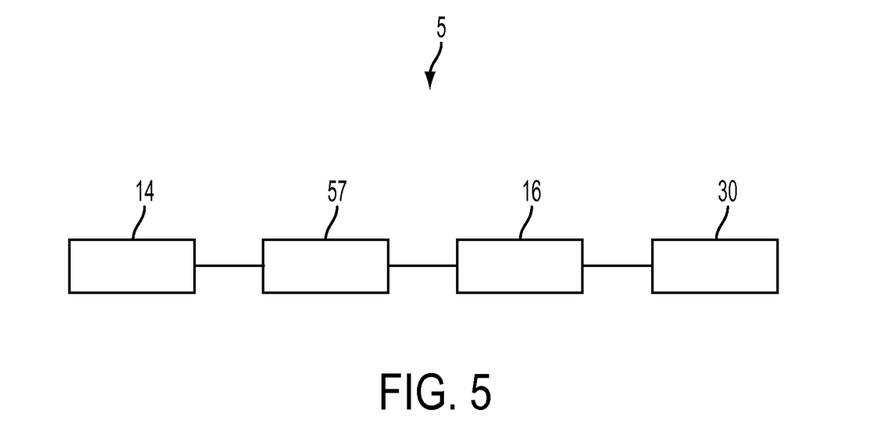
FIG. 5: A schematic diagram of an illustrative illumination device according to one or more embodiments herein.
Figure 6:
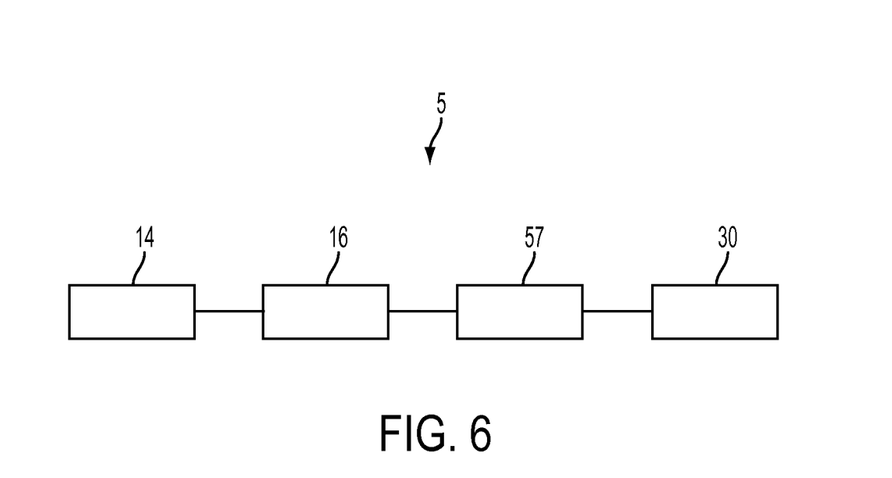
FIG. 6: A schematic diagram of an illustrative illumination device according to one or more embodiments herein.
Figure 7:
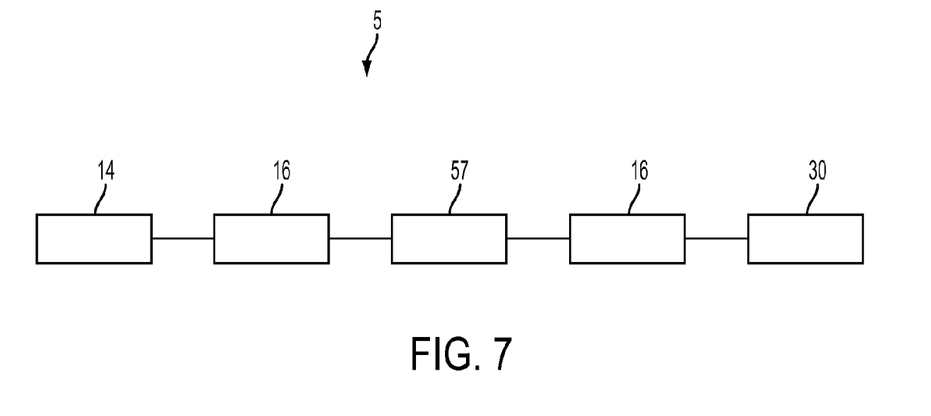
FIG. 7: A schematic diagram of an illustrative illumination device according to one or more embodiments herein.

Referring to FIGS. 5, 6 and 7, additional examples of illumination device 5 are shown and described. The illumination device 5 may be optically connected to, or be used in conjunction with the wavelength selective devices 16 to selectively transmit electromagnetic radiation in a particular range of wavelengths such as, for example, visible light, while blocking certain other wavelengths such as, for example UV and/or NUV. Such wavelength selective device 16 when optionally being used with a medical diagnostic and examination illumination devices 5 and instruments of the present disclosure may permit the transmittance of visible light while preventing the transmittance of the UV and/or NUV light from the illumination device 5 to a specimen 57. Alternatively, the wavelength selection device 16 may also be designed to transmit or pass through only or a portion of the UV and/or NUV light from the LED 14, while blocking the emission of all or a portion of the visible light, to stimulate the auto-fluorescence and measure such auto-fluorescence in the skin, eye, or ear to assist in medical diagnostics.

The illumination device 5 may be configured to produce digital images or digital imaging of the specimen 57. The illumination device 5 may be coupled to an imager 30. The coupling may be optically and/or electrically coupling or the illumination device 5 may be used in conjunction with the imager 30. Examples of the imager 30 may include digital imaging devices such as a digital camera and/or other image sensors. In some embodiments, the imager 30 (e.g., digital camera) may include a charge-coupled device ("CCD") and/or a complimentary metal-oxide semiconductor ("CMOS"). In another embodiment, the illumination device 5 may be optically and/or electrically connected to one CCD and/or CMOS sensors. It is understood that the imager 30 as shown in FIGS. 4, 5, and 6 may be the human eye, a camera, digital camera, digital sensors (e.g., CCD, CMOS), projector, film, display, other imaging device, and/or combinations thereof. Furthermore, it should be understood that more than one of the imager 30 may be coupled to the illumination device 5 as for example where an image is projected and produced on film.

FIG. 7 depicts the illumination device 5 may comprise the wavelength selective device 16 disposed before and/or after the specimen 57 where each wavelength selection device 16 may permit different particular range of wavelengths to pass through. Such an illumination device 5 would be operable to change the color of the electromagnetic radiation emitted from the LED 14 and/or to block visible light to measure auto-fluorescence. For example the first wavelength selection device 16 may filter harmful UV electromagnetic radiation and illuminate the specimen 57 with the remaining spectrum and the second wavelength selection device 16 may filter part of the visible spectrum to emphasize certain wavelengths for the imager 30.

In another embodiment, one or more of the illumination device 5 may be used to perform a fluorescein angiography or fluorescent angiography. Fluorescein angiography or fluorescent angiography is a technique for examining the circulation of the retina using the dye tracing method. It involves injection of sodium fluorescein into the systemic circulation, and then an angiogram is obtained by photographing the fluorescence emitted after illumination of the retina with blue light at a specific wavelength, e.g., 490 nanometers. In one example, the illumination device 5 may comprise the composition of phosphor coated on the UV and/or NUV LED (, e.g., LED 14) of the illumination device 5 tuned through the composition of phosphors to emit electromagnetic radiation in order to perform the fluorescein angiography procedure. In another example, the illumination device 5 may comprise the composition of a phosphor coating on the UV and/or NUV LED, wherein the electromagnetic radiation emitted is across a much broader range of the electromagnetic spectrum of wavelengths than just the specific wavelength necessary to perform the procedure, but may includes the wavelength selection device 16 in the form of an interference bandpass filter (e.g., exciter filter or barrier filter) that blocks out all electromagnetic radiation but a specific wavelength such as, for example, 490 nm, which is necessary to perform the fluorescein angiography procedure. Exciter filters allow only blue light to illuminate the retina. Depending on the specific filter or the wavelength selection device 16, the excitation wavelength hitting the retina will be from about 465 to about 490 nm. Many exciter filters may only allow light through at a wavelength of 490 nm. Barrier filters allow only yellow-green light (from the fluorescence) to reach the imager 30 (e.g., camera, eye), skin, ear, etc. Barrier filters generally only allow light from about 520 nm to about 530 nm, but many only allow light with a wavelength of about 525 nm. It should be understood that more than one imager 30 may be used.

Figure 8:
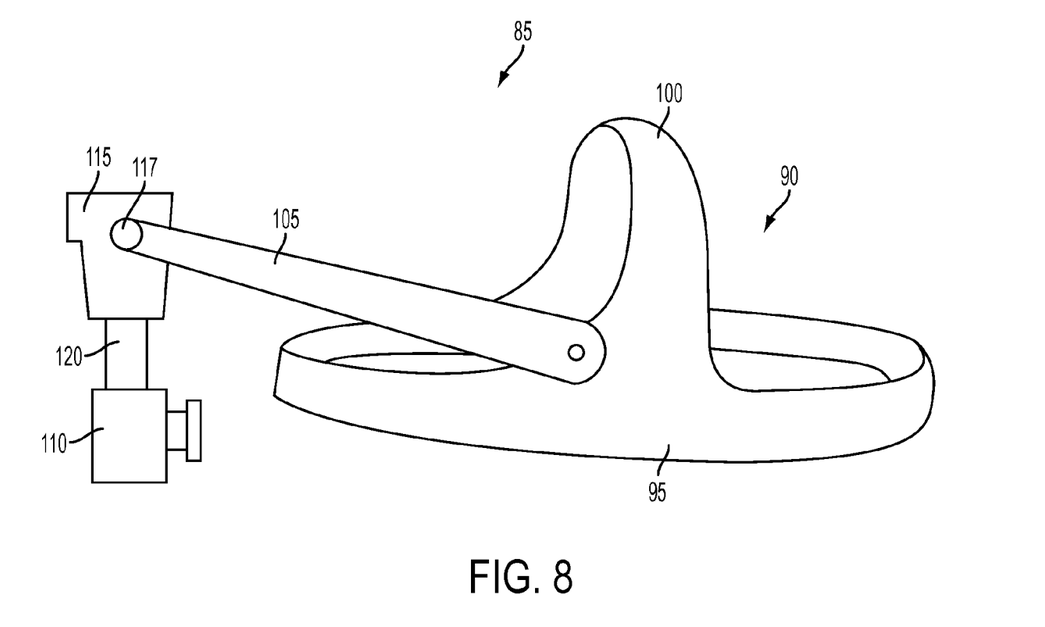
FIG. 8: A schematic diagram of an illustrative indirect binocular ophthalmoscope according to one or more embodiments herein.

Referring to FIG. 8, a binocular indirect ophthalmoscope 85 is shown. The binocular indirect ophthalmoscope 85 includes an adjustable head assembly 90, which may be worn on the head of a doctor using the binocular indirect ophthalmoscope 85 in a manner similar to a conventional indirect ophthalmoscope. The adjustable head assembly 90 may have a head band 95 for encircling the head, a strap 100 integral with head band 95 adapted to fit on top of the head, and a semi-circular band 105 pivotally attached to the sides of the head band 95 and extending toward the front end thereof. The viewing assembly 110 below an illumination assembly 115 may be secured to the forward part of semi-circular band 105 by a coupling attachment 117 or other suitable means. Although the semi-circular band 105 is rigidly secured, it may be pivoted up or down with reference to head band 95 so as to adjust the vertical position of the viewing assembly 110.

The housing of illumination assembly 115 has a tube 120 or other similar means extending downwardly therefrom into the viewing assembly 110 which is provided with means therein for permitting binocular vision when the observer's eyes are optically aligned with the viewing assembly 110. The illumination assembly 115 may include elements of the illumination device 5, such as, for example, LED 14 pumped with UV and/or NUV electromagnetic radiation as shown and described above, emitting in a predetermined electromagnetic radiation spectrum. It is understood that multiple LED's 14 may be used, depending on the desired application.

Figure 9:
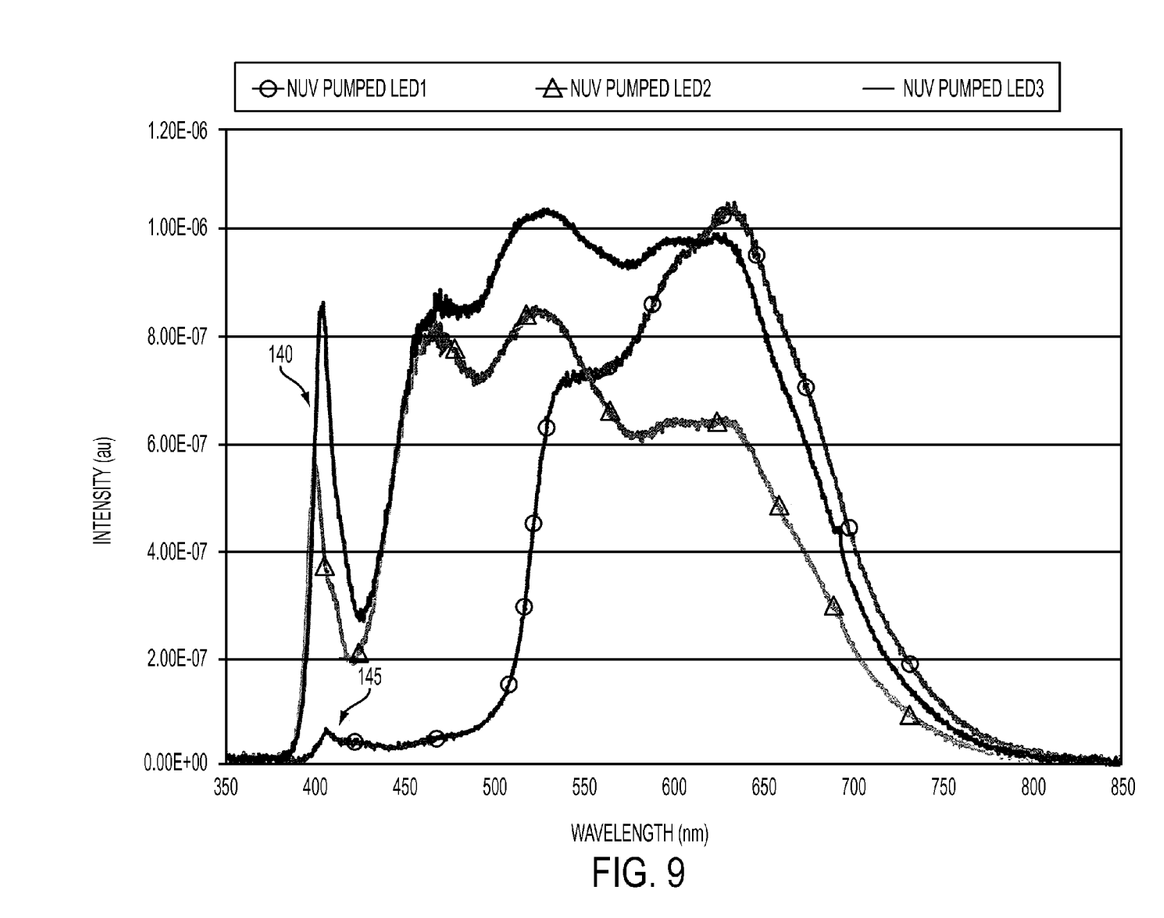
FIG. 9: A plot graphically the electromagnetic spectrum of several different NUV pumped LEDs coated with a composition of phosphors.

FIG. 9 graphically illustrates the electromagnetic spectrum of several different NUV pumped LEDs coated with different compositions of red, green, and blue phosphor. The composition of phosphors and mixtures were different in "NUV Pumped LED 1" (circle marker), "NUV Pumped LED 2" (triangle marker), and "NUV Pumped LED 3" (no marker), illustrating how different electromagnetic wavelength characteristics could be achieved by changing the phosphor characteristics to achieve different color temperatures and/or to enhance or change the contrast for various medical devices. "NUV Pumped LED 3" illustrates a relatively "flat" distribution of electromagnetic radiation across the visible spectrum. A peak 140 is illustrative of the NUV wavelength used to pump the LED 14. A weak peak 145 is also illustrative of the filtering properties of the wavelength selection device 16. As described above, the NUV wavelength could be filtered to produce the weak peak 145 by the mixture of the composition of phosphors of "NUV Pumped LED 1" or as a separate device.

Figure 10:
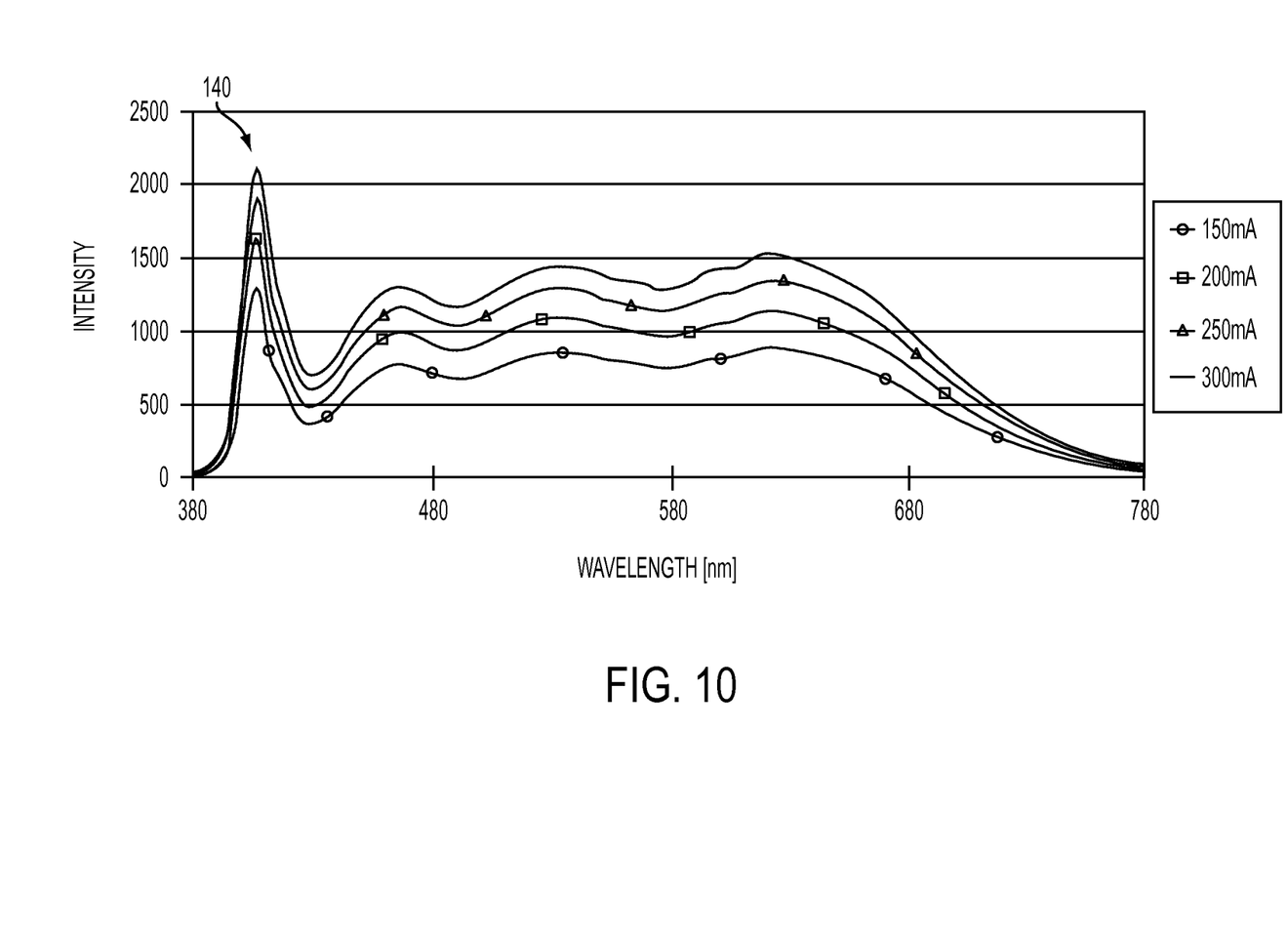
FIG. 10: A plot graphically illustrates the electromagnetic spectrum of a single composition of phosphors on a NUV pumped LED at varying electrical currents.

FIG. 10 graphically illustrates the electromagnetic spectrum of a single composition of phosphors on a NUV pumped LED at varying electrical currents. If more optical power is needed, then more UV and/or NUV LED's 14 of FIG. 3 may be added and/or more electrical current may be provided to the illumination device 5. At 150 milliamps (closed circle marker), the electromagnetic spectrum is relatively flat for the compositions of phosphors across the visible spectrum. As the current is increased from 150 milliamps to 300 milliamps (no marker), the electromagnetic spectrum starts to emphasize the wavelengths of the dominant phosphors in the composition of phosphors on the LED 14. The intermediate currents at 200 milliamps (square marker) and 250 milliamps (closed triangle marker) illustrate the shift from the relatively flat electromagnetic spectrum at 150 milliamps to the emphasized wavelengths at 300 milliamps. The current of the LED 14 is a consideration for medical diagnostic equipment and the resulting electromagnetic spectrum. As described in FIG. 9, the peak 140 of FIG. 10 is indicative of the NUV wavelength used to pump the LED 14.

As set for herein, the UV and/or NUV pumped LED's or lasers may act as a light source for a variety of equipment, instruments, and/or medical diagnostic and/or examination procedures, including but not limited to general medical lighting (e.g., surgical lights, examination room lighting, focused examination lighting, etc.), retinal imaging devices, otoscopes, ophthalmoscopes (e.g., manual ophthalmoscopes, slit lamps, stereo ophthalmoscopes, direct ophthalmoscopes, indirect ophthalmoscopes, combinations thereof, etc.), and dermascopes.

It should be understood that in any of the illustrative examples of the illumination device 5 shown and described above herein, the LED 14 may comprise blue light rather than UV and/or NUV as, for example, electromagnetic energy having wavelength from about 440 nm to about 490 nm. The composition of phosphors coating the blue pumped LED 14 may be adjusted to achieve the desired CRI, R9, CQS, and/or other illumination properties. The blue pumped LED 14 may be combined with any of the other components as shown and described herein to perform the illumination methods as shown and described herein. The illustrative embodiments of the illumination device 5 shown and described herein may include one or more of the LED 14 comprising blue light.

In certain illustrative examples of the illumination device 5, conventional illumination devices may be fitted or retrofitted with the UV and/or NUV LED's as shown and described herein without modification or with use of simple adaptors. In other embodiments, conventional instruments may also be slightly modified or redesigned to incorporate the UV and/or NUV LED's if needed as well. If UV and/or NUV LED adaptors or retrofitting of existing instruments is impractical, designs of new instruments utilizing the UV and/or NUV LED or UV and/or NUV laser are envisioned.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An illumination device comprising:
   at least one light emitting diode emitting electromagnetic radiation with a wavelength from about 200 nanometers to about 440 nanometers, the electromagnetic radiation is emitted along a path;
   a composition of phosphors coating the at least one light emitting diode comprising a red phosphor, yellow phosphor, a blue phosphor, a green phosphor, an orange phosphor, a violet phosphor, or combinations thereof;
   at least one wavelength selection device positioned in the path to selectively permit electromagnetic radiation of a particular range of wavelengths to pass through;
   a mirror to change a direction of the path;
   at least one lens to diverge the electromagnetic radiation, wherein the at least one wavelength selection device, the mirror, and the at least one lens are disposed in the path; and
   a housing wherein the at least one light emitting diode, the at least one wavelength selection device, the mirror, and the at least one lens are attached to and within the housing.

2. The device of claim 1, further comprising at least one imager coupled to the illumination device.

3. The device of claim 2, wherein the at least one imager may be a camera, a digital camera, a projector, or film.

4. The device of claim 1, wherein the particular range of wavelengths is from about 200 nanometers to about 380 nanometers.

5. The device of claim 1, wherein the particular range of wavelengths is from about 380 nanometers to about 750 nanometers.

6. The device of claim 1, wherein the light emitting diodes are clustered in an array.

7. The device of claim 6, wherein the array is selected from the group consisting of a linear array, a stagger array, a herringbone array, a honeycomb array, a triangular array, a hexagonal array, and a circular array.

8. The device of claim 1, wherein the composition of phosphors are modified to produce a Color Rendering Index of greater than 80%.

9. The device of claim 8, wherein the composition of phosphors are modified to produce the Color Rendering Index of greater than about 97%.

10. The device of claim 9, wherein the composition of phosphors are modified to produce the Color Rendering Index of greater than about 98%.

11. The device of claim 10, wherein the composition of phosphors are modified to produce the Color Rendering Index of greater than about 99%.

12. The device of claim 11, wherein the composition of phosphors are modified to produce the Color Rendering Index of about 100%.

13. The device of claim 1 wherein the composition of phosphors are modified to absorb electromagnetic radiation with a wavelength from about 200 nanometers to about 440 nanometers.

14. The device of claim 1, wherein the illumination device is a scope selected from the group consisting of an ophthalmoscope, otoscope, and dermascope.

15. The device of claim 1, wherein the at least one wavelength selection device is a filter selected from the group consisting of a dichroic filters, dichroic mirrors, dichroic reflectors, reflective filters, thin film filters, interference filters, gel film filters, band pass filters, interference bandpass filters, and combinations thereof.

16. The device of claim 1, wherein the composition of phosphors are red, green, and yellow.

17. The device of claim 1, wherein the composition of phosphors are red, green, and blue.

18. A method of illuminating a specimen comprising:
    emitting electromagnetic radiation along a path with a wavelength from about 200 nanometers to about 440 nanometers using at least one light emitting diode, wherein a composition of phosphors coats the at least one light emitting diode comprising a red phosphor, yellow phosphor, a blue phosphor, a green phosphor, an orange phosphor, a violet phosphor, or combinations thereof;
    selectively permitting electromagnetic radiation of a particular range of wavelengths to pass through at least one wavelength selection device disposed in the path;
    changing a direction of the path using a mirror; and
    diverging the electromagnetic radiation using a lens, wherein the at least one wavelength selection device, the mirror, and the lens are disposed in the path.

19. The method of claim 18, wherein the particular range of wavelengths is from about 200 nanometers to about 380 nanometers.

20. The method of claim 18, wherein the particular range of wavelengths is from about 380 nanometers to about 750 nanometers.

21. The method of claim 18, wherein the composition of phosphors are red, green, and yellow.

22. The method of claim 18, wherein the composition of phosphors are red, green, and blue.

23. A method of producing electromagnetic radiation comprising:
    illuminating a specimen using an illumination device comprising:
    at least one light emitting diode emitting electromagnetic radiation with a wavelength from about 200 nanometers to about 440 nanometers along a path,
    a composition of phosphors coating the at least one light emitting diode comprising a red phosphor, yellow phosphor, a blue phosphor, a green phosphor, an orange phosphor, a violet phosphor, or combinations thereof, at least one wavelength selection device positioned in the path to selectively permit the electromagnetic radiation of a particular range of wavelengths to pass through, a mirror to change a direction of the path, a lens to diverge the electromagnetic radiation, wherein the at least one wavelength selection device, the mirror, and the lens are disposed in the path, and a housing wherein the at least one light emitting diode, the at least one wavelength selection device, the mirror, and the lens are attached within the housing; and actuating an adjustment wheel to change the particular range of wavelengths permitted by the at least one wavelength selection device.

24. The method of claim 23, wherein the particular range of wavelengths is from about 200 nanometers to about 380 nanometers.

25. The method of claim 23, wherein the particular range of wavelengths is from about 380 nanometers to about 750 nanometers.

26. The method of claim 23, wherein the composition of phosphors are red, green, and yellow.

27. The method of claim 23, wherein the composition of phosphors are red, green, and blue.

* * * * *